(12) United States Patent
Kiss

(10) Patent No.: US 7,011,965 B2
(45) Date of Patent: Mar. 14, 2006

(54) COMPOSITIONS AND METHODS FOR STIMULATING WOUND HEALING AND FIBROBLAST PROLIFERATION

(75) Inventor: Zoltan Kiss, Austin, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/873,654

(22) Filed: Jun. 4, 2001

(65) Prior Publication Data

US 2002/0127216 A1   Sep. 12, 2002

Related U.S. Application Data

(60) Provisional application No. 60/274,852, filed on Mar. 9, 2001.

(51) Int. Cl.
*C12N 9/00* (2006.01)

(52) U.S. Cl. .................................. 435/183
(58) Field of Classification Search .............. 424/94.6; 435/183
See application file for complete search history.

(56) References Cited

U.S. PATENT DOCUMENTS

| | | | |
|---|---|---|---|
| 4,030,995 A | * | 6/1977 | Starkweather |
| 4,265,233 A | * | 5/1981 | Sugitachi et al. |
| 4,556,056 A | * | 12/1985 | Fischer et al. |
| 4,818,540 A | | 4/1989 | Chien et al. |
| 5,487,889 A | * | 1/1996 | Eckert et al. |
| 5,707,624 A | * | 1/1998 | Nickoloff et al. |
| 6,265,436 B1 | * | 7/2001 | Appere et al. |
| 6,290,952 B1 | * | 9/2001 | Poelstra et al. |

FOREIGN PATENT DOCUMENTS

| | | | |
|---|---|---|---|
| DE | 3007226 | * | 9/1981 |
| JP | 60117919 | * | 12/1986 |
| SU | 1138410 | * | 2/1985 |
| SU | 1814764 | * | 3/1995 |
| WO | WO 92/14480 | * | 9/1992 |

OTHER PUBLICATIONS

Altruis Biomedical Network, Growth Factor.net, 2002, 1-3.*
Beck and Burtscher, "Expression of Human Placental Alkaline Phosphatase in *Escherichia coli*," *Protein Expression and Purification*, 1994, 5:192-197.
Carmichael et al., "Evaluation of a Tetrazolium-based Semiautomated Colorimetric Assay: Assessment of Chemosensitivity Testing," *Cancer Res.*, 1987, 47:936-942.
Chang et al., "Modification of human placental alkaline phosphatase by periodate-oxidized 1, $N^6$—ethenoadenosine monophosphate," *Biochem. J.*, 1990, 272:683-690.
Chang et al., "Human placental alkaline phosphatase," *Eur. J. Biochem.*, 1992, 209:241-247.
Heimo et al., "Human Placental Alkaline Phosphatase: Expression in *Pichia pastoris*, Purification and Characterization of the Enzyme," *Protein Expression and Purification*, 1998, 12:85-92.
Millán and Fishman, "Biology of Human Alkaline Phosphatases with Special Reference to Cancer," *Crit. Rev. Clin. Lab. Sci.*, 1995, 32(1):1-39.
She et al., "Placental alkaline phosphatase, insulin, and adenine nucleotides or adenosine syndergistically promote long-term survival of serum-starved mouse embryo and human fetus fibroblasts," *Cellular Signalling*, 2000, 12:659-665.
She et al., "Growth factor-like effects of placental alkaline phosphatase in human fetus and mouse embryo fibroblasts," *FEBS Letters*, 2000, 469:163-167.

* cited by examiner

*Primary Examiner*—Michael Meller
(74) *Attorney, Agent, or Firm*—Fish & Richardson P.C., P.A.

(57) ABSTRACT

It has been found that placental alkaline phosphatase interacts synergistically with growth factors and corresponding serum factors to stimulate the proliferation of adult fibroblast cells. Furthermore, this stimulation of fibroblast proliferation does not result in a corresponding stimulation of collagen synthesis. Thus, wound healing compositions can be formulated that improve wound healing without increasing scar formation. Compositions for wound healing can include placental alkaline phosphatase and a gel-forming material. In some embodiments, compositions include placental alkaline phosphatase and serum/growth factors. In addition to wound healing applications, compositions with placental alkaline phosphatase can also be used in cell culturing of adult fibroblast cells.

12 Claims, 13 Drawing Sheets

COMPOSITIONS AND METHODS FOR STIMULATING WOUND HEALING AND FIBROBLAST PROLIFERATION

The present application is based on and claims the benefit of U.S. Provisional Patent Application Ser. No. 60/274,852, filed Mar. 9, 2001, the content of which is hereby incorporated by reference in its entirety.

BACKGROUND OF THE INVENTION

This invention relates to compositions and methods to stimulate wound healing. More particularly, this invention relates to the use of compositions including placental alkaline phosphates for stimulating wound healing.

People afflicted with long-term illness run the risk of getting bed sores, pressure sores and a myriad of skin irritations and chronic wounds. Cancer patients, in particular breast cancer patients, treated with radiation face the risk of skin burns. Wound healing after surgical intervention has been historically problematic. The benefits of surgery, even in life threatening situations, are offset by the formation of disfiguring scar tissue. Adult wound healing is characterized by fibrosis, scarring, and sometimes by contracture.

Fibroblast cells, located in the dermal layer, play important roles in wound healing by, for example, producing components of the extracellular matrix like collagen and various cytokines, which, in turn, enhance the proliferation and migration of keratinocytes. Keratinocytes are located in the epidermal layer and form a barrier against the external environment.

Healing of wounds is the results of interplay among different cell types and various growth factors. Some of the growth factors, including platelet-derived growth factor (PDGF), epidermal growth factor (EGF), fibroblast growth factor (FGF), transforming growth factor α (TGF-α) and insulin like growth factor I (IGF-I), are considered to play significant roles by enhancing proliferation of fibroblasts and/or keratinocytes while TGF-β appears to primarily act via increasing matrix formation.

Normal wound healing is also characterized by the production of collagen. In adult skin, fibroblasts present at the wound site usually produce more collagen than necessary for optimal healing due to the stimulatory actions of TGF-β and PDGF. Excess collagen then leads to the undesirable formation of scar tissue.

SUMMARY OF THE INVENTION

In a first aspect, the invention pertains to a composition for wound healing in a patient comprising placental alkaline phosphatase and a gel-forming material.

In another aspect, the invention pertains to a composition for stimulating cell proliferation comprising placental alkaline phosphatase and a proliferation compound. In these embodiments, the proliferation compound is selected from the group consisting of a growth factor, a growth promoting serum factor and mixtures thereof.

In further aspects, the invention pertains to a method for accelerating wound healing applying a composition to the wound, the composition comprising placental alkaline phosphatase.

In addition, the invention pertains to a method for stimulating proliferation of cells in a cell culture. The method includes contacting the cells with a composition comprising a cell culture medium, placental alkaline phosphatase and a proliferation compound selected from the group consisting of a growth factor and a growth promoting serum factor.

DETAILED DESCRIPTION OF THE PREFERRED EMBODIMENTS

Figure 1:
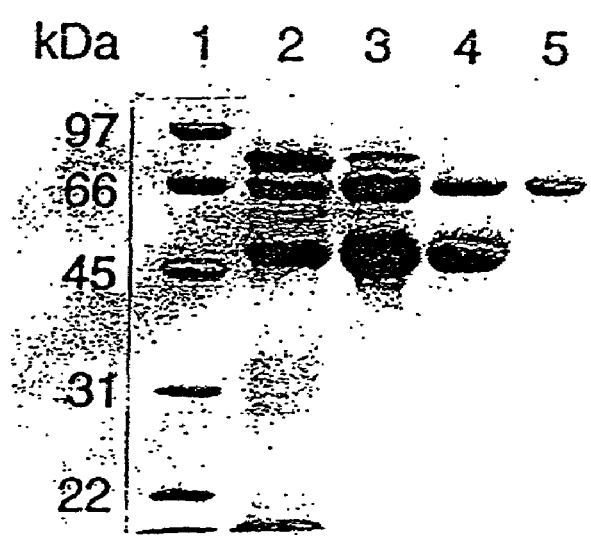
FIG. 1 is a picture of a coommassie stained gel with purified placental alkaline phosphatase (PALP).

Beneficial compositions that include placental alkaline phosphatase (PALP) can stimulate viability and proliferation of fibroblasts. Particularly when the PALP compositions are used in vitro for cell culture applications, the compositions can also include one or more proliferation compounds, which can be growth factors or growth promoting serum factors. Proliferation compounds synergistically combine with PALP to stimulate adult fibroblast proliferation and are referred to below as serum/growth factors. Serum/growth factors are optional when the PALP composition is used for in vivo wound healing applications, although use of serum/growth factors may be preferred. PALP compositions, when applied to a wound, are expected to accelerate the viability and the proliferation of the fibroblasts at the wound site resulting in accelerated wound healing.

PALP is an evolutionary new member of the alkaline phosphatase group of enzymes that hydrolyze phosphate-containing compounds and are reviewed in McLomb et al., "Alkaline Phosphatases," (Plenum Press, New York, 1979) and Millan and Fishman, "Biology of human alkaline phosphatases with special reference to cancer," Critical Tev. Clin. Sci., 22: 1–39 (1995), both of which are incorporated herein by reference. PALP is synthesized by human and primate placentas. PALP can exhibit growth factor-like effects in fetal fibroblasts, such as human fetal fibroblasts and mouse embryo fibroblasts. See, for example, She et al. (2000) FEBS Letters, 469, p.163–167 and She et al. (2000) Cell. Signal. 12, p.659–665, both of which are incorporated herein by reference. In the present approaches, contrary to earlier work, it has been discovered that PALP, in combination with serum/growth factors, stimulate proliferation of adult fibroblasts, in particular adult skin fibroblasts. Without the serum/growth factors, PALP evidently does not significantly stimulate adult fibroblasts proliferation.

Agents that enhance the viability and numbers of fibroblasts can exert promoting effects on wound healing. In addition, PALP can enhance the proliferation of fibroblasts without exerting a stimulatory effect on collagen synthesis. PALP compositions may be used on a variety of patients for wound healing, and the expectation is that healing incorporating PALP compositions will cause less scarring than growth factors alone. The patient can be an animal, especially a mammal. Preferably, the patient is human, canine, porcine, bovine or the like.

Both semi-purified placenta extracts and highly purified PALP preparations can be used as active components in compositions aimed at accelerating proliferation of fibroblasts. In vivo, semi-purified placenta extracts enriched in PALP or highly purified PALP preparations may accelerate the viability and proliferation rate of fibroblasts at wound sites. Specifically, in the presence of natural serum and/or added growth factors, PALP is expected to induce a synergistic effect on fibroblast growth resulting in accelerated wound healing without a corresponding stimulation of collagen formation.

In addition, PALP-containing compositions can be useful for improving in vitro cell culturing of adult fibroblast cells. In vitro, the presence of growth factors or growth promoting serum factors, however, is necessary for accelerating the viability and proliferation rate of adult fibroblasts. Serum/growth factors, as referred to herein, include agents that enable cells to move from stationary phase to the proliferative phase. As shown in the Examples below, the combination of PALP and serum/growth factors result in a synergistic effect on adult fibroblast proliferation.

PALP compositions generally include PALP and a non-toxic carrier or vehicle. For wound healing applications, the preferred form of the PALP composition is a gel. For either in vivo or in vitro applications, PALP compositions may include additional serum/growth factors to increase the proliferation of the fibroblasts. In addition, PALP compositions can include one or more additives/enhancers, such as preservatives, buffers, moisture control compounds and/or antibiotics. PALP compositions generally include sufficient PALP to stimulate proliferation of fibroblasts for the particular application.

The PALP compositions preferably enhance viability and proliferation of skin fibroblasts. The fibroblasts can be postnatally derived skin fibroblasts and/or embryonic fibroblasts. The PALP composition generally do not stimulate proliferation of keratinocytes.

In wound healing, shortly after skin is wounded, various growth factors, including, for example, PDGF, TGF-$\beta$1, and other growth factors can be detected in the wounded tissue. Collagen synthesis can also occur at a wound site. An excess of collagen synthesis, however, can result in the formation of undesirable scar tissue at a wound site. Application of a PALP composition to the wounded tissue is expected to accelerate wound healing via stimulation of fibroblast growth. It has also been discovered that PALP can also decrease, rather than increase, collagen synthesis by fibroblasts in the presence of one or more growth factors, for example, PDGF and/or TGF-$\beta$1. PALP compositions may, thus, accelerate wound healing with less scar formation. In contrast, if PDGF is applied alone for wound healing, in addition to stimulating cell proliferation, the PDGF also stimulates collagen production that should lead to enhanced scarring.

In order to accelerate wound healing, PALP compositions can be applied to a wound. The PALP compositions can be applied in a variety of ways including, but not limited to, direct application to the wound. Since serum/growth factors can be detected at a wound site as part of the natural wound healing process, addition of exogenous, i.e., non-native, progression factors, either included in the PALP composition or as a separate composition, can be optional for wound healing.

The PALP compositions described herein may be used to stimulate healing of a variety of wounds. PALP compositions can be applied to external wounds including, for example, those caused by surgery, cuts, bruises, burns, sores and the like. PALP compositions may also be applied to internal organs, for example, during surgery. PALP compositions may also be beneficial for cosmetic applications to enhance wound healing with less scarring.

Generally, the use of a composition that accelerates wound healing is desirable, because it would result in (i) reduction of period of discomfort, (ii) shorter stay in the hospital after major surgeries (resulting in major cost savings), (iii) decreased potential for infections, (iv) faster recovery after cosmetic surgery, and (v) overall reduction in sick leaves due to major wounds.

PALP Products

PALP products are PALP compositions formulated for specific applications. The PALP products described herein include PALP and may include other active ingredients, such as serum/growth factors and other additives. The PALP products generally also include a non-toxic carrier or the like to facilitate use of the PALP product. The nature of the PALP product including the types and amounts of both active ingredients and inactive carriers depend on the intended use of the PALP product. The PALP product can be used for in vivo wound healing or in vitro cell culturing.

PALP products can include placental material containing PALP, a semi-purified PALP preparation, a highly purified PALP preparation, recombinant PALP and the like. Human PALP is a protein, specifically, an enzyme found in the human placenta. PALP is a member of the group of alkaline phosphatase enzymes that hydrolyze phosphate containing compounds at alkaline pH values. At neutral pH they are observed to hydrolyze phosphatidic acid and some other substrates.

Natural PALP is observed to be a dimer of two identical glycosylated polypeptide subunits. The primary source of PALP is a placenta, which synthesizes this enzyme in latter stages of pregnancy, i.e. during approximately the second and third trimester of pregnancy in humans. At term in humans, PALP becomes a major alkaline phosphatase in circulation. PALP has been cloned and overexpressed in several cell lines, as described in Millan and Fishman, "Biology of human alkaline phosphatases with special reference to cancer," Critical Tev. Clin. Sci. 22:1–39 (1995), incorporated herein by reference. Production of recombinant PALP has been difficult so far, although low yields have been obtained in *Escherichia Coli* (see Beck and Burtsch, "Expression of human placental alkaline phosphatase in *Escherichia coli,*" Protein Expression and Purification 5:192–197 (1994), incorporated herein by reference) and yeast *Pichia pastoris* (see Heimo et al., "Human placental alkaline phosphatase:Expression in *Pichia pastoris,* purification and characterization of the enzyme," Protein Expression and Purification 12:85–92 (1998), incorporated herein by reference).

Semi-purified PALP preparations can be obtained, for example, from Sigma Chemical Co. St. Louis, Mo. The semi-purified PALP can be used to form PALP products or can be used to obtain highly purified PALP. Highly purified PALP from human placenta can be obtained by successive chromatographic separations, as described further in Example 1 below.

The concentration of PALP in a PALP product can have various values and generally depends on the specific use. For in vivo wound healing applications, the concentration may also depend on the location and type of wound, and the individual on whom it is used. Generally, the concentration of PALP in a wound healing product can be at least about 0.001 mg/1 g product, preferably between about 0.01 and about 0.5 mg/1 g product and more preferably, between about 0.01 and about 0.1mg/1 g product.

For in vitro cell culture applications, a PALP product can be included with a cell culture media or, alternatively, diluted into a cell culture media by addition to a culture. The concentration of PALP in a PALP product for cell culture applications may depend on the anticipated dilution into a cell culture medium, if any, prior to use in the cell culture. In actual cell culture use, a cell culture medium preferably includes PALP at a concentration at least about 0.001 milligrams/milliliter (mg/ml), preferably from about 0.01 to about 0.5 mg/ml, and more preferably from about 0.01 to about 0.1 mg/ml. More concentrated PALP products for dilution into a cell culture media can have a concentration calculated based on the values for the cell culture media based on the desired dilution value. In preferred embodiments, the concentrated PALP product for dilution into a cell culture medium has a concentration from about 0.01 to about 10 mg/ml and preferably from about 0.1 to about 1 mg/ml.

PALP products may include one or more serum/growth factors. Growth factors that can be included in PALP products include, for example, platelet-derived growth factor (PDGF), epidermal growth factor (EGF), fibroblast growth factor (FGF), transforming growth factor α (TGF-α), insulin-like growth factor I (IGF-I), transforming growth factor-β1 (TGF-β1) and insulin.

The serum/growth factors may augment the PALP effects by activating the fibroblast cells from a stationary phase in a cell cycle, referred to as $G_o$ cycle, to a proliferative phase, referred to as $G_{1-m}$ cycle. PALP products may also include any other agent that can induce cells into the proliferative phase.

The composition may include one growth factor, preferably PDGF. Alternatively, the composition may include two growth factors, preferably PDGF and insulin. More than two growth factors can be included.

The concentration of the serum/growth factors in a PALP product, if used, can vary depending on the specific growth factor used, the specific use of the composition, the nature of the wound and the like. Generally, the concentration of the serum/growth factor in a PALP product can be between about 5 nanogram/milliliter (ng/ml) and about 1000 ng/ml. Preferably, the concentration of the serum/growth factors in the PALP composition is between about 25 ng/ml and about 250 ng/ml, and more preferably, the concentration is between about 50 ng/ml and about 150 ng/ml.

To incorporate growth promoting serum factors, a PALP product may include whole serum, as a composite of growth factors. Serum can be from a variety of sources, for example, fetal calf serum (FCS). Serum is generally obtained during blood fractionation and is known in the art. Specifically, serum generally is a blood product with cells and cell fragments removed. Serum may also include serum fractions that have undergone other purification steps while retaining a complex mixture of compounds.

Serum is generally sterile or is sterilized prior to addition to the composition. In embodiments for proliferating fibroblasts in vitro, FCS is particularly preferable. For in vitro proliferation, the final concentration of the serum in the cell culture can be between about 0.1 percent by volume and about 20 percent by volume. Preferably, the final concentration of the serum in the cell culture is between about 0.5 percent by volume and about 12 percent by volume, more preferably, between about 1 percent by volume and about 10 percent by volume.

One or more isolated serum factors may also be included in the PALP product. Serum factors, referred to herein, are components that are normally found in the serum. Serum factors can include, for example, growth factors, and other growth promoting agents, such as lysophosphotidic acid (LPA). It should be noted that tests have indicated that PALP and LPA do not promote each other's effects on fibroblast growth. Isolated serum factor/s can be included in the PALP products to enhance PALP effects. The concentration of the serum factors in the PALP products, if used, can vary dependent on the specific serum factor and the specific use of a PALP product.

Additives/enhancers in PALP compositions may include various ingredients, for example, preservatives (such as parabenes, quartinary ammonium compounds, alcohol, phenols, essential oil and the like), buffers, antioxidants (such as vitamine E), antimicrobials, vitamins, and moisture control agents (such as glycerine, propylene glycol, and the like). Other potential additives include, for example, analgesics, anesthetics, anti-acne agents, anti-dermatitis agents, anti-pruritic agents, anti-inflammatory agents, anti-hyperkeratolytic agents, antiperspirants, anti-psoriatic agents, anti-seborrheic agents, anti-aging agents, anti-wrinkle agents, skin lightening agents, depigmenting agents, corticosteroids, additional tanning agents or hormones. These additives may have some desirability in wound healing formulations.

For wound healing applications, the PALP products can also include pharmaceutically and/or cosmetically acceptable carriers or vehicles. Preferably, the carriers are non-toxic. A pharmaceutically acceptable carrier does not cause an adverse physical reaction upon administration and is one in which PALP is sufficiently soluble to deliver a therapeutically effective amount of PALP. The therapeutically effective amount of PALP may vary based on the individual patient, the indication being treated and other criteria evident to one of ordinary skill in the art. A therapeutically effective amount of PALP is one sufficient to induce repair, healing and restoration of the target tissue to the original strength.

Similarly, a cosmetically acceptable carrier is one that does not cause an adverse physical reaction upon application to the wound site and one in which PALP is sufficiently soluble to deliver a cosmetically effective amount of PALP. The cosmetically effective amount of PALP may vary based on the individual patient, the indication being treated and other criteria evident to one of ordinary skill in the art. A cosmetically effective amount of PALP is one sufficient to induce repair, healing or augmentation of a target tissue with minimal scar tissue.

As used herein, "pharmaceutical" or "cosmetic" will be understood to encompass both human and animal pharmaceuticals or cosmetics. Carriers and vehicles can be included in the PALP products in order to obtain an appropriate consistency, for example, gels, lotions, cream, rinse and the like. These products are suitable as topical compositions for wound healing applications.

Suitable carriers generally include, for example, water, acetone, ethanol, ethylene glycol, propylene glycol, butane-1,3-diol, isopropyl myristate, isopropyl palmitate, mineral oil, mixtures thereof and the like. Buffered solutions can also serve as carriers. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton, Pa. 1990, incorporated herein by reference.

In embodiments for topical applications, the carrier may be in any form appropriate for topical application to the skin including, for example, solutions, colloidal dispersions, emulsions (oil-in-water or water-in-oil), suspensions, creams, lotions, gels, foams, mousses, sprays and the like. PALP compositions suitable for use in topical application may also include, for example, liposomal carriers suspended in a suitable base or vehicle. Any liquid, pharmaceutically acceptable vehicle in which PALP is at least minimally soluble is suitable for topical use in the present invention. Other preparations that may be suitable include application of the composition onto a polyvinyl alcohol sponge.

For wound healing applications, the PALP products are preferably a gel. In some suitable embodiments, the gel includes methyl cellulose, agar, agarose, gelatin, calcium algenate or combinations thereof to form the gel. For example, the PALP after sterile filtration can be incorporated into sterile 3% by weight methyl cellulose gel, 1% by weight agarose gel, 4% by weight gelatin gel or 1–3% by weight calcium algenate. Generally, the PALP solution is sterile filtered and added to the gel formers in a sterile room. Wounds can be dressed with PALP gel and covered with gauze, which can be anchored with elastic adhesions.

The PALP composition can be stored under aseptic conditions at 4° C. Since PALP is stable at even room temperature and since growth factors and other typical additives are stable for several weeks at 4° C., the formulations should remain fully active for at least about 3 weeks.

The present invention provides compositions suitable for transdermal administration. Such compositions are applied directly to the skin or incorporated into a protective carrier such as a transdermal device, i.e. a patch. Examples of suitable creams, ointments, or the like, can be found, for example, in the Physician's Desk Reference. Examples of suitable transdermal devices are described in, for example, U.S. Pat. No. 4,818,540 to Chien et al. entitled "Transdermal Fertility Control System And Process," incorporated herein by reference.

For cell culture applications, the nature of the carrier just has to be consistent with subsequent inclusion in a cell culture medium. Generally, for dilution into a cell culture medium, the carrier is an aqueous solution, and can be sterilized water or a buffer. PALP can also be stored as a powder. The PALP, in whatever form obtained, can be directly added to a cell culture medium or directly formulated into a cell culture medium.

The cell culture medium should be suitable for culturing adult fibroblast cells. Suitable cell culture media for culturing adult fibroblast cells are known in the art. In particular, commercial cell culture media for culturing adult fibroblast cells are available, as described in the Examples below.

Other additives may also include, for example, water soluble colorants, oil soluble colorants, water soluble sunscreens, oil soluble sunscreens, particulate sunscreens, chelating agents, emulsion stabilizers, preservatives, fragrances, flavoring agents, humectants, waterproofing agents, water soluble film-formers, oil-soluble film formers, cationic polymers, anionic polymers, viscosity modifying agents, mixtures thereof, and the like.

PALP compositions can be made using any number of suitable techniques. In some embodiments, PALP and a carrier can be mixed together within a commercial mixer to form a solution, a suspension or the like. In cosmetic and/or pharmaceutical composition embodiments, methodologies for formulation are well known, and can be found, for example, in Remington's Pharmaceutical Sciences, Eighteenth Edition, A. R. Gennaro, Ed., Mack Publishing Co. Easton, Pa. 1990, incorporated herein by reference.

The PALP compositions can be additionally processed after synthesis for purification, sterilization and the like. Sterilization, for example, can be conducted by filter sterilization, irradiation and the like. Methods for conducting these steps are known in the art and can be found, for example, in Remington's Pharmaceutical Sciences, Eighteenth Edition, A. R. Gennaro, Ed., Mack Publishing Co. Easton, Pa. 1990, incorporated herein by reference.

Stimulation of Fibroblast Proliferation and Wound Healing

The PALP products/compositions described herein can be used for increasing the viability and proliferation of cells, particularly fibroblasts. The PALP compositions are intended to be used, in vivo, in patients to accelerate wound healing. Furthermore, the PALP composition may be used for wound healing to reduce the amount of scar tissue formed at a wound site in a patient. In addition, the PALP compositions can be used in vitro in fibroblast cell cultures.

In vitro, the PALP compositions can be used in the presence of one or more serum/growth factors to stimulate viability and proliferation of fibroblasts. Cells are contacted with the PALP compositions for a period of time in the presence of growth stimulating factors, such as serum and/or growth factors. The PALP compositions are added to the cell culture medium to provide the necessary contact with the cells to stimulate cell proliferation.

The order of combining the components of the cell culture medium with the PALP composition and the progression factors generally is not significant. For example, the PALP compositions can be added directly to the cell cultures containers such as cell culture plates or flasks. The serum may be included in the PALP composition. Alternatively, the serum may be provided separately to the cell culture container before, during or after addition of the PALP composition. Alternatively, the PALP composition, the serum/growth factors or both can be combined with the cell culture medium prior to addition to the cell culture container. A combination of these approaches can be used to obtain a desired PALP concentration and serum/growth factor concentration with the passage of time during the cell culture process.

In in vitro embodiments, the cells are contacted with the PALP composition and serum/growth factors for selected amount of time to stimulate cellular proliferation. Preferably, the cells are contacted with the PALP composition for at least about one day. In other embodiments, the cells are contacted with the PALP composition for at least about 3 days and, for example, between about 3 days and about 6 days. In other embodiments, the cell cultures are maintained continuously in the presence of the PALP composition. During the cell culturing process, the cells are maintained in suitable conditions, such as temperature and oxygenation, to provide appropriate conditions for cell viability and proliferation. Appropriate cell culturing conditions are well known in the art.

To promote wound healing, the PALP composition, or PALP alone, can be applied to a wound either directly or indirectly. Routes of administration include, for example, topical, transdermal, parenteral, and gastrointestinal. Direct routes of applying PALP compositions to a wound are topical and involve contacting the PALP composition directly to the wound. Transdermal administration can be accomplished by application of a cream, rinse, gel and the like that are capable of allowing the PALP to penetrate the skin. Parenteral administration can include, for example, electrical or direct injection such as intravenous, intramuscular, intraperitoneal or subcutaneous injection. Gastrointestinal approaches involve oral injection of a composition.

Topical administration can be accomplished via a topically applied cream, rinse, gel and the like that include PALP in the composition. In some embodiments, the creams, ointments and the like containing PALP can be delivered by dressings, bandages or other similar coverings capable of releasing a therapeutic amount of PALP. Such dressings can be directly placed on the wound to promote healing. Other methods of delivering the PALP compositions are also within the scope of this invention. The therapeutic amount of PALP that is necessary to be delivered to the wound site can vary and depend on the specific wound, the location of the wound, the patient and the like.

The PALP composition can be administered to the wound for a suitable amount of period. Suitable period is generally for at least one day. Suitable period can be for at least about 3 days. In some embodiments, PALP compositions may be administered to a wound for at least about a week. In other embodiments involving chronic problems, the PALP compositions may be administered for several months or more.

The PALP composition can be administered as needed. Alternatively, PALP compositions can be administered two or more times a day. The frequency of administration of the PALP composition can vary and depend on the type of wound, the location of the wound, the concentration of the PALP in the composition and the method used to administer the PALP composition. Generally, a therapeutically effective amount of PALP composition is administered. A medical professional supervising treatment can adjust administered doses to obtain desired results.

Storage, Packaging and Distribution

The PALP products can be stored, preferably at about room temperature if they do not contain other serum/growth factors or preferably at about 4° C. if they do contain another serum/growth factor. Preferred storage techniques minimize the risk of contamination and maintain the stability of the product. Following a final sterilization step, the sterile PALP product is transferred only using sterile transfer techniques, or the PALP product is sterilized in the container that is sealed for sterile storage and/or transportation of the PALP product for distribution. For cell culture applications, maintaining sterile conditions is also important.

Appropriate packaging generally depends on the intended use of the PALP product. For cell culture applications, the PALP product generally is stored in a container for easy administration to a cell culture system in the form desired. For wound healing applications, the packaging generally depends on the form of the product. Ointments and the like can be stored in tubes or the like. Liquid solutions can be stored in sealed vials. Capsules or the like for oral injections can be stored in sterile jars or the like.

For distribution, the PALP composition can be placed in a sterile, sealed container. The containers are generally dated such that the date reflects the maximum advisable storage time considering possible degradation of the PALP as well as other factors. The containers are packaged along with instructions for the proper use of the composition and along with appropriate and/or required labeling. The containers can be distributed to individuals or health care professionals for use in appropriate medical procedures. Similarly, the compositions can be distributed for use in cell cultures.

EXAMPLES

Example 1

Purification of Human PALP

This example relates to the preparation and characterization of purified human PALP.

A partially purified preparation of PALP (Type XXIV human PALP with 1020 units of total activity) was purchased from Sigma Chemical Co., St. Louis, Mo. As determined by SDS polyacrylamide gel electrophoresis, the commercial PALP was not homogeneous. A butanol extraction of the placenta was performed by Sigma Chemical to obtain the partially purified preparation. The butanol extraction inactivates most of the other placental proteins, including growth factors, but does not reduce either the mitogenic or the enzymatic activity of PALP.

A 350 mg quantity of commercial PALP was dissolved into 10 ml of buffer A (0.1 M sodium acetate, 0.5 M NaCl, 1 mM $MgCl_2$, 1 mM $CaCl_2$ at pH 6.5). The partially purified human PALP preparation was further purified first by successive Concanavalin A-Sepharose and Q-Sepharose column chromatography. The Concanavalin A-Sepharose column was run using buffer A as the solvent. For elution, buffer A included 50 mM α-methyl-D-mannopyranoside. The active fractions were pooled and dialyzed against buffer B (50 mM tris-HCL at pH 7.7). After dialysis, the protein was passed through a Q-sepharose column. The protein was eluted with buffer B using a linear gradient of 0–250 mM potassium phosphate at a pH of 7.5. The active fractions from the Q-sepharose column were pooled and dialyzed against phosphate-buffered saline and concentrated by Amicon ultrafiltration.

Then, the purified PALP fraction off the Q-Sepharose column (which still contained 2 major proteins) was purified to homogeneity by t-butyl hydrophobic interaction chromatography (HIC). Prior to adding the protein to the t-butyl HIC column, the solution was made 2M in ammonium sulphate, and the pH was adjusted to 6.8. The 5 ml bed volume t-butyl HIC cartridge (Bio-Rad) was connected to a FPLC system (Pharmacia). The column was eluted with buffer C (100 mM sodium phosphate buffer, 2M ammonium sulphate at pH 6.8). The column was eluted with buffer C until a first protein peak completely eluted, and then a negative gradient of 2M-0M ammonium sulphate in 100 mM sodium phosphate at pH 6.8 was passed over the column. The negative linear gradient was used to elute a second enzymatically active peak. Following dialysis against phosphate buffered saline and concentration, purity of the enzyme was confirmed by SDS PAGE gel electrophoresis. A single protein band was observed with an approximate molecular weight of 55–60 kD. The gel following separation was stained using coommassie blue for visual observation of protein bands. The purification procedure is described further in Chang et al. (1992) Eur. J. Biochem. 209, 241–247, incorporated herein by reference.

PALP enzyme activity was assayed spectrophotometrically by monitoring the hydrolysis of 4-nitrophenylphosphate (as an increase in absorbance at 410 nm) at room temperature (22° C.). The analysis was performed with 1 ml volume containing 50 mM $Na_2CO_3$/$NaHCO_3$, 10 mM $MgCl_2$, 10 mm 4-nitrophenylphosphate at pH 9.8. The assay is described further in Chang et al. (1990) Biochem. J. Vol. 272, pp.683–690, incorporated herein by reference. The extinction coefficient of 4-nitrophenol was taken as $1.62 \times 10^4$ $M^{-1}$ $cm^{-1}$. An enzyme activity of 1 U (unit) is defined as 1 μmol substrate hydrolyzed/min at 22° C. at pH 9.8.

FIG. 1 shows a picture of a coommassie stained gel. The gel includes partially purified Sigma PALP preparation (shown in lane 2) further purified by successive Concanavalin A-Sepharose (lane 3), Q-Sepharose (lane 4), and t-butyl HIC chromatography (2 M-0 M ammonium sulphate gradient) (lane 5). Lane 1 shows the molecular mass standards. Separation of proteins was performed by conventional sodium dodecyl sulfate-polyethylene amine gel electrophoresis (SDS-PAGE) and proteins were stained by coommassie blue stain.

FIG. 1 demonstrates that while the Sigma preparation contains 3 major proteins (one of them is PALP while an approximately 52 kDa protein band is $α_1$-antitrypsin) and several minor proteins, the purified preparation apparently contains only PALP. Identification of the PALP band by sequence analysis was performed by the Mayo Clinic Protein Core Facility (Rochester, Minn., USA). Although the purified PALP preparation did not seem to contain any other protein, the possibility of minor protein contaminants cannot be ruled out. But this possibility does not diminish the usefulness of the purified PALP.

Examples Showing the Effects of PALP on Human Cell Lines

In the following examples, the effects of PALP and other factors on human cell lines are examined. The following materials were used in these examples.

Partially purified human PALP was purchased and purified as described in Example 1. (3-4,5-dimethylthiazol-2-yl)-2,5-diphenyltetrazolium bromide (MTT) was purchased from Sigma Chemical Co., St. Louis, Mo. Insulin (INS) and all the other growth factors used here were purchased from Boehringer Mannheim, Indianapolis, Ind. [Methyl-$^3$H]thymidine (500 mCi/mmol) was purchased from Dupont NEN, Boston, Mass. Tissue culture reagents, including Dulbecco's modified Eagle's medium (DMEM) and fetal calf serum (FCS) were purchased from GIBCO-BRL (Rockville, Md.).

Human skin fibroblast cell lines were purchased from American Type Culture Collection. The cell lines, CCD 39 SK, CCD 986 SK, CCD 1058 SK, CCD 974 SK, CCD 944 SK, and CCD 966 SK, were derived respectively from one week old, 22 year old, 52 year old, 61 year old, 66 year old, and 78 year old subjects. Each cell line, maintained in 10% FCS-containing DMEM, was used between 4–7 passages after thawing.

Example 2

Effect of PALP on Proliferation of Skin Fibroblasts and DNA Synthesis

This example relates to the effect of PALP on a skin fibroblast culture and on the amount of DNA synthesis in the fibroblast culture.

Figure 2:
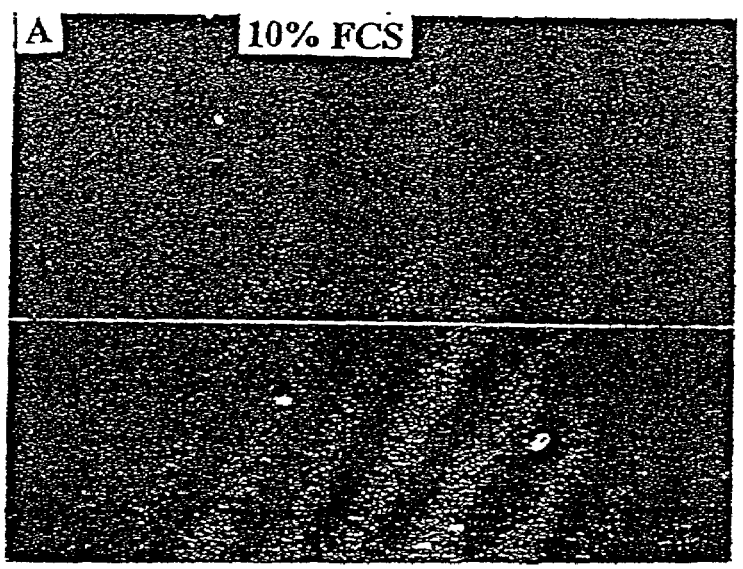
FIG. 2 is a picture of microplate wells with human skin fibroblasts incubated with fetal calf serum and with and without PALP.
Figure 2:
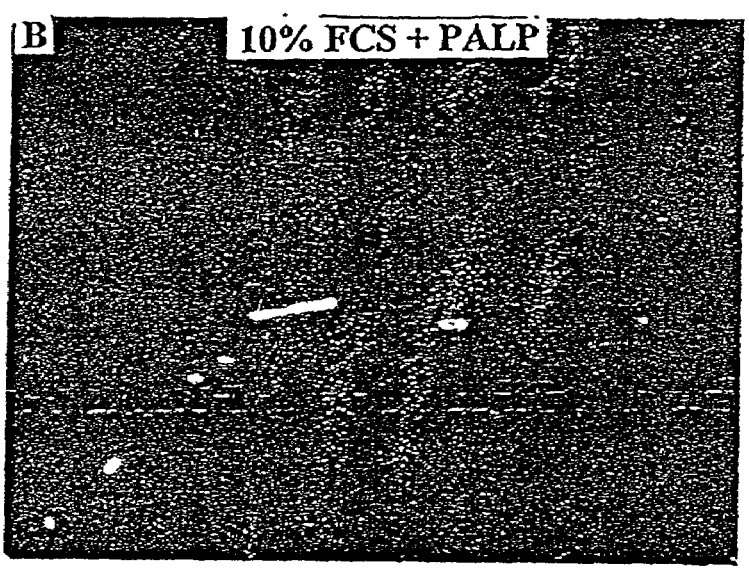

CCD 1058 SK human skin fibroblasts were seeded at $3 \times 10^4$ cells/well (12-well microplate) and then incubated in 10% FCS-containing DMEM for 4 days in the absence (upper panel) or presence (lower panel) of 2 Unit/ml purified PALP. The visual results are shown in FIG. 2. Visual inspection of this and similar pictures clearly gave the impression that PALP treatment increased the number of fibroblasts. Initial visual analysis was followed by collection of quantitative data, including measurement of DNA synthesis and cell proliferation, as described in the following examples.

Example 3

DNA Synthesis

This example describes the increased DNA synthesis from fibroblast cells resulting from PALP use.

CCD 1058 SK human skin fibroblasts were serum-starved (27 h) and then incubated for 18 h in the absence of serum (A) or in the presence of 2% FCS (B). During the incubation, the fibroblasts were untreated or treated with 1 Unit/ml purified PALP, 500 nanomolar (nM) insulin (INS) and 3.8 millimolar (mM) total $Ca^{2+}$ alone or in combinations as indicated.

For the determination of DNA synthesis, human skin fibroblasts were grown in 12-well tissue culture dishes to about 40–50% confluency in 10% fetal calf serum (FCS)-containing DMEM, washed, and then incubated in serum-free medium for 27 h. The cells were washed and then treated for 17 h in serum-free medium with PALP in the absence or presence of INS and/or calcium ($Ca^{2+}$), followed by incubation for 1 h in the presence of [$^3$H]thymidine (1 μCi/well). At this point, cells in each well were sub-confluent. In these experiments, PALP was added to the cells 10 and 20 min prior to $Ca^{2+}$ and INS, respectively. However, PALP was similarly effective when it was added 20 min prior to or 10 min after insulin. The cells were washed twice with PBS, then four times with 5% trichloroacetic acid, and finally twice with absolute ethanol. The acid-insoluble material, which contained [$^3$H]thymidine-labeled DNA, was redissolved in 0.3 M sodium hydroxide and then $^3$H activity was counted. Using this procedure, all [$^3$H] activity is associated with DNA.

Figure 3:
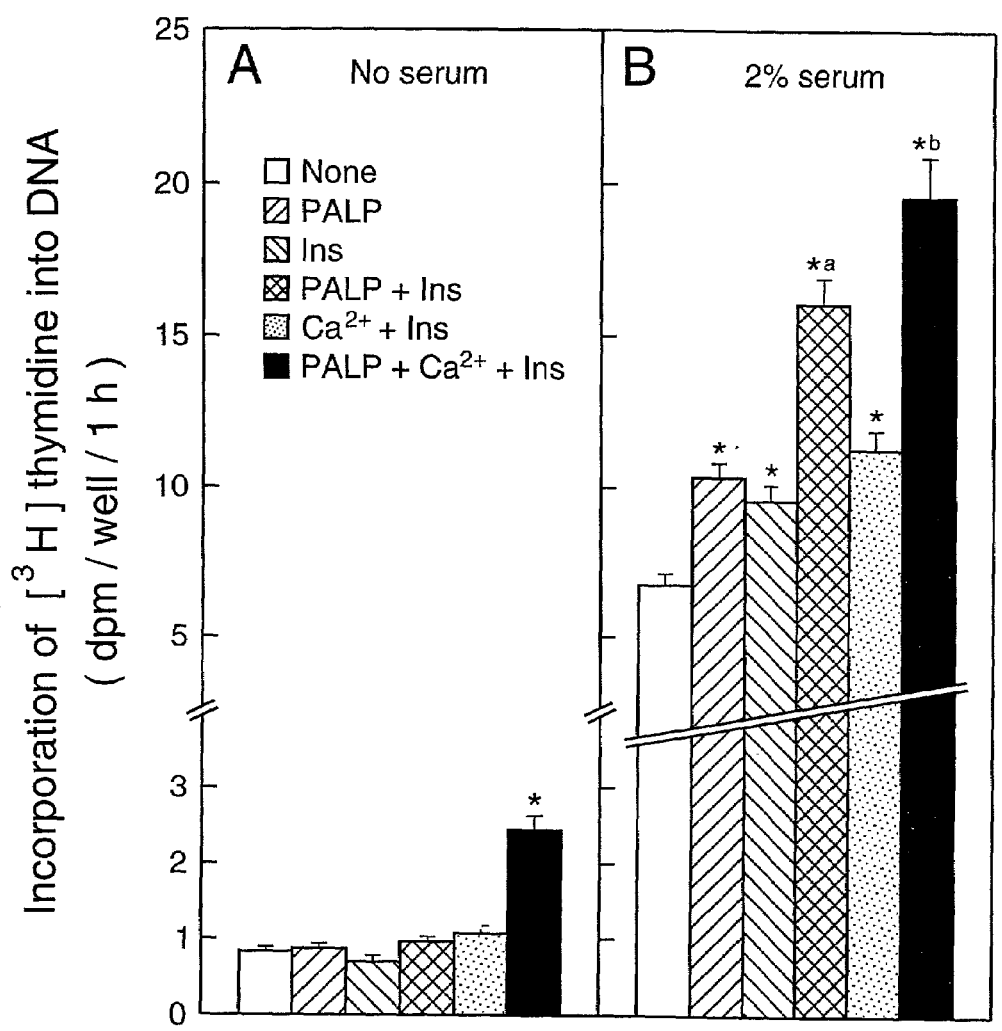
FIG. 3 is a plot of DNA synthesis in human skin fibroblasts in the presence and absence of serum. Responses with PALP, INS and/or calcium are shown.

FIG. 3 shows the results of DNA synthesis in fibroblasts. Data are the means±S.E.M. (standard error of means) of three experiments each performed in triplicate. On the plot shown in FIG. 3, the asterisks indicate the following: *significantly ($P<0.01$ level) greater values than the value with no addition of additional factors; *$^a$significantly ($P<0.01$ level) greater values than obtained with PALP or INS alone; *$^b$significantly ($P<0.01$ level) greater values than the combined effects of $Ca^{2+}$ and INS. The last value is the same as the effect of $Ca^{+2}$ alone, which are not shown.

The data indicate that in the absence of serum, the presence of both high concentration of $Ca^{2+}$ and INS is required for the stimulatory effect of PALP on DNA synthesis, while in the presence of serum, PALP also had stimulatory effect in the absence of $Ca^{2+}$ and INS. Cell viability/proliferation was measured directly using MTT analysis, as described in the following example.

Examples 4–12

Cell Viability/Proliferation Measurements

These examples examine the quantitative effects on cell proliferation as a result of adding PALP with or without other factors to cell cultures of human fibroblasts.

(MTT Assay) For the determination of Cell Viability/Proliferation, fibroblasts were seeded at 1000 cells/well in 96-microwell plates in 10% FCS-containing DMEM. After 24 h, the medium was replaced with 1, 2, or 10% serum-containing fresh medium followed by treatments with PALP and growth factors for 3 or 6 days; in the latter case, after 3 days of treatments, the medium was changed for fresh (respective) medium followed by re-treatment of cells. At the time of analysis, cells in each well were subconfluent. The relative changes in the number of viable cells were determined by MTT assay. This calorimetric assay is based on the ability of healthy cells (mostly the mitochondrial compartment) to reduce MTT to a blue formazan product. A Labsystem Multiskan MS microplate reader purchased from Labsystemes (Franklin, Mass.) was used to measure the formation of formazan as an increase in absorbance at a test wavelength of 540 nm and a reference wavelength of 690 nm. This technique is a widely used and accepted method to accurately determine the relative numbers of viable cells. In most cases, when the test agent does not strongly influence the oxidation-reduction balance of cells, the MTT assay is essentially a proliferation assay. The MTT assay is described further in Carmichael et al. (1987) Cancer Res. 47, p.936–942, incorporated herein by reference.

In the data analysis, data were either mean values±one standard deviation (S.D.) (3–8 independent incubations from the same experiment; for evaluating significance, Student's t test is used) or mean values±S.E.M. of three experiments (3 incubations in each; for evaluating significance, unpaired t test is used). Each experiment presented here was repeated at least once with similar results.

Example 4

Combination of PALP and Insulin

This example shows the effect of combining purified PALP and insulin on fibroblast cell proliferation after either 3 days of incubation and after 6 days of incubation.

Figure 4:
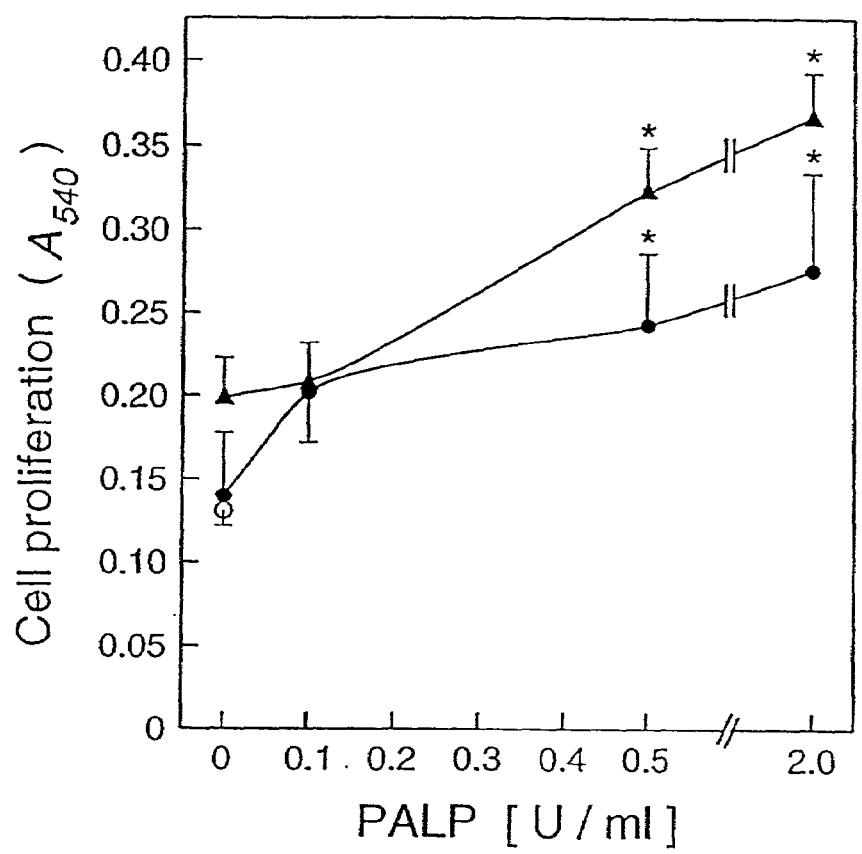
FIG. 4 is a plot of the effect of PALP concentration on cell proliferation after 3 days of incubation.

In a first set of experiments, CCD 1058 SK human skin fibroblasts cells, incubated in 2% FCS-containing DMEM for 3 days, were treated with 0–2 Unit/ml purified PALP, as indicated, in the absence (●) or presence (▲) of 500 nM INS during the entire incubation period. The incubation period was followed by an MTT assay. FIG. 4 shows a plot of MTT assay results. Data are means±S.D. of 8 incubations. As indicated in FIG. 4 with an "*", significantly (P<0.01 level) greater values were obtained with the addition of PALP in comparison with the corresponding values in the absence of PALP. This experiment showed that 0.5–2.0 Unit/ml PALP increased the number of CCD 1058 SK fibroblasts both in the absence and presence of INS during a 3 day incubation period. However, PALP and insulin had greater effects in combination than alone.

Figure 5:
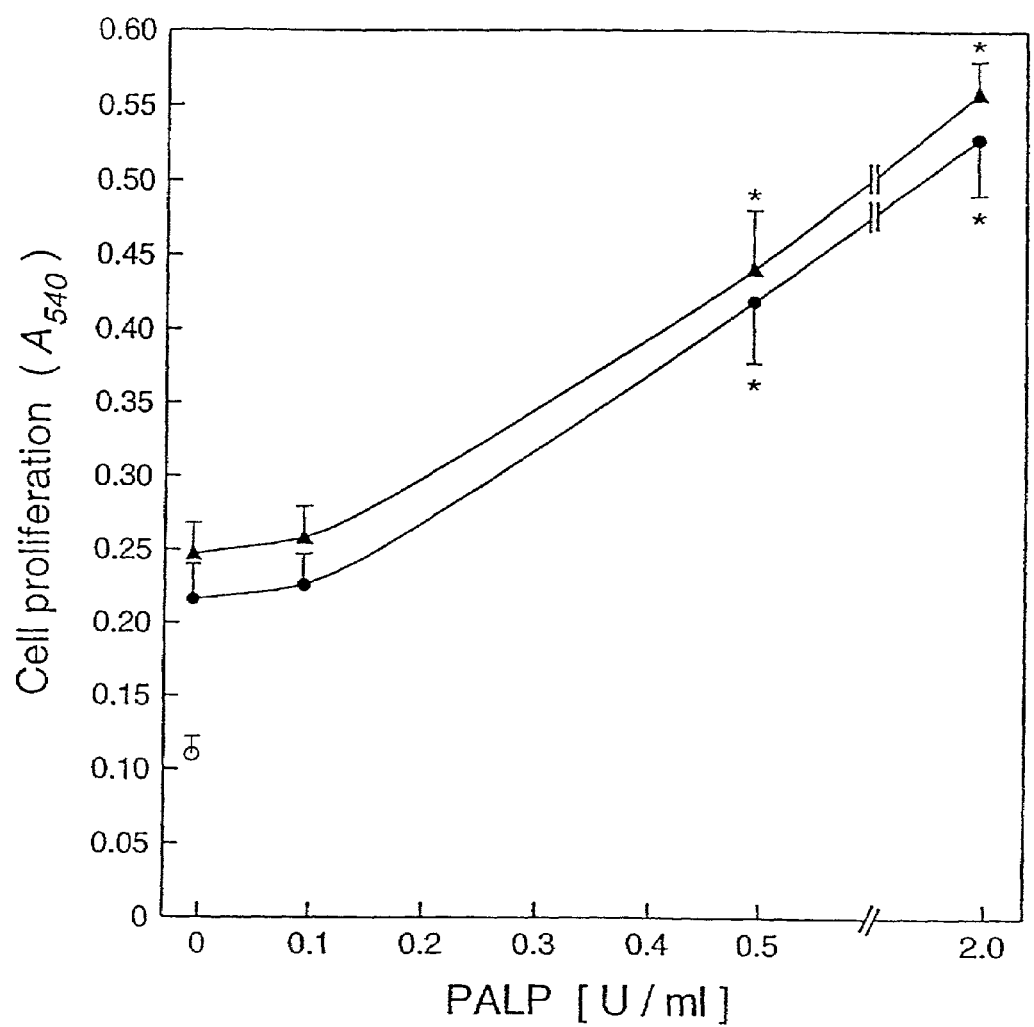
FIG. 5 is a plot of the effect of PALP concentration on cell proliferation after 6 days of incubation.

In another experiment, CCD 1058 SK human skin fibroblasts cells, incubated in 2% FCS-containing DMEM for 6 days, were treated with 0–2 Unit/ml purified PALP, as indicated, in the absence (●) or presence (▲) of 500 nM INS during the entire incubation period. This was followed by the MTT assay. FIG. 5 shows a plot of the assay results. Data are means±S.D. of 8 incubations. As noted in FIG. 5 with an "*", significantly (P<0.01 level) different values were obtained for the samples with added PALP from the corresponding values in the absence of PALP.

This experiment showed that 0.5–2.0 Unit/ml PALP increased the number of CCD 1058 SK fibroblasts both in the absence and presence of INS even if the incubation period was extended to 6 days. In the presence of 2% FCS, PALP and INS had no cumulative or synergistic effects on cell proliferation.

In the total absence of serum, PALP did not enhance proliferation of CCD 1058 SK fibroblasts (not shown). In contrast, in mouse embryo fibroblasts (NIH 3T3), PALP stimulated DNA synthesis and cell proliferation even in the absence of serum. In further experiments, in the absence of serum, PALP did not enhance cell proliferation in any of the other human skin fibroblast lines examined in this application.

Example 5

Partly Purified PALP and Insulin

This example demonstrates that even partly purified PALP can be effective to stimulate fibroblasts in cell culture when combined with other agents.

Figure 6:
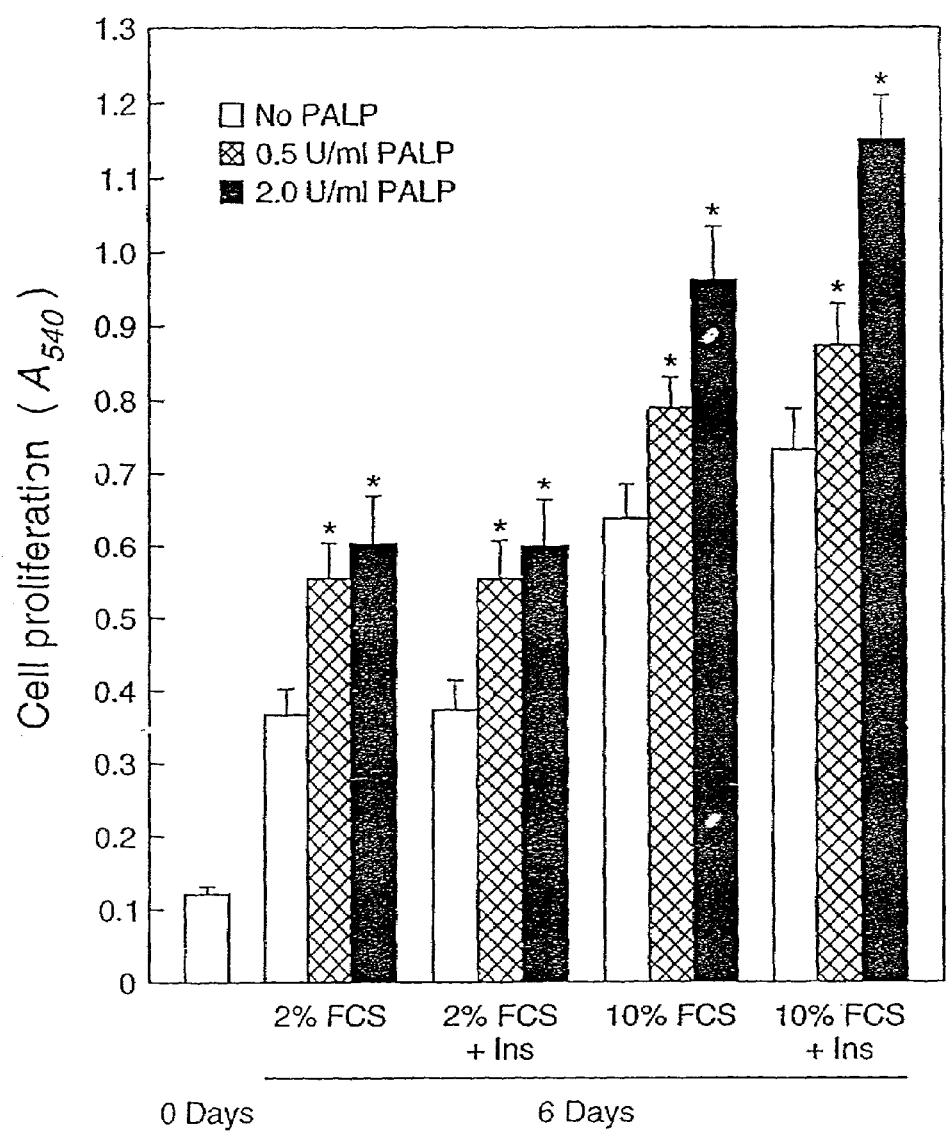
FIG. 6 is a plot of the effect of partially purified PALP, concentration of PALP and concentration of serum on cellular proliferation.

CCD 1058 SK human skin fibroblast cells were treated for 6 days with no PALP (□), or with 0.5 Unit/ml Sigma PALP (☒), or with 2 Unit/ml Sigma PALP (■) in the presence of 2% or 10% FCS with or without 500 nM INS, as indicated. This was followed by the MTT assay. FIG. 6 shows a plot of the assay results. Data were the means±S.D. of 8 incubations. As indicated in FIG. 6 with an "*", significantly (P<0.01–0.05 level) greater proliferation was measured in sample with PALP than the corresponding values measured in the absence of Sigma PALP.

This experiment demonstrated that partially purified PALP also increases proliferation of CCD 1058 SK fibroblasts in the presence of 2–10% serum±INS. Therefore, for the same effect, a partially purified PALP preparation may be used instead of highly purified PALP.

Example 6

Effect of PALP Combined with Different Factors in One Human Skin Fibroblast Cell Line.

This example relates to determining the effect of PALP, alone and in combination with other factors, on the viability and proliferation of the CCD 39 SK skin fibroblast cell line.

CCD 39 SK human skin fibroblasts, incubated in 1% FCS-containing DMEM for 6 days, were untreated (□) or treated (■) with 0.5 Unit/ml Sigma PALP in the absence or presence of PDGF (50 ng/ml), epidermal growth factor (EGF) (50 ng/ml), basic fibroblast growth factor (bFGF) (20 ng/ml), transforming growth factor-α (TGF-α) (50 ng/ml), TGF-β1 (5 ng/ml), insulin-like growth factor I (IGF-I) (50 ng/ml) or INS (500 nM), as indicated. The incubation was followed by an MTT assay.

Figure 7:
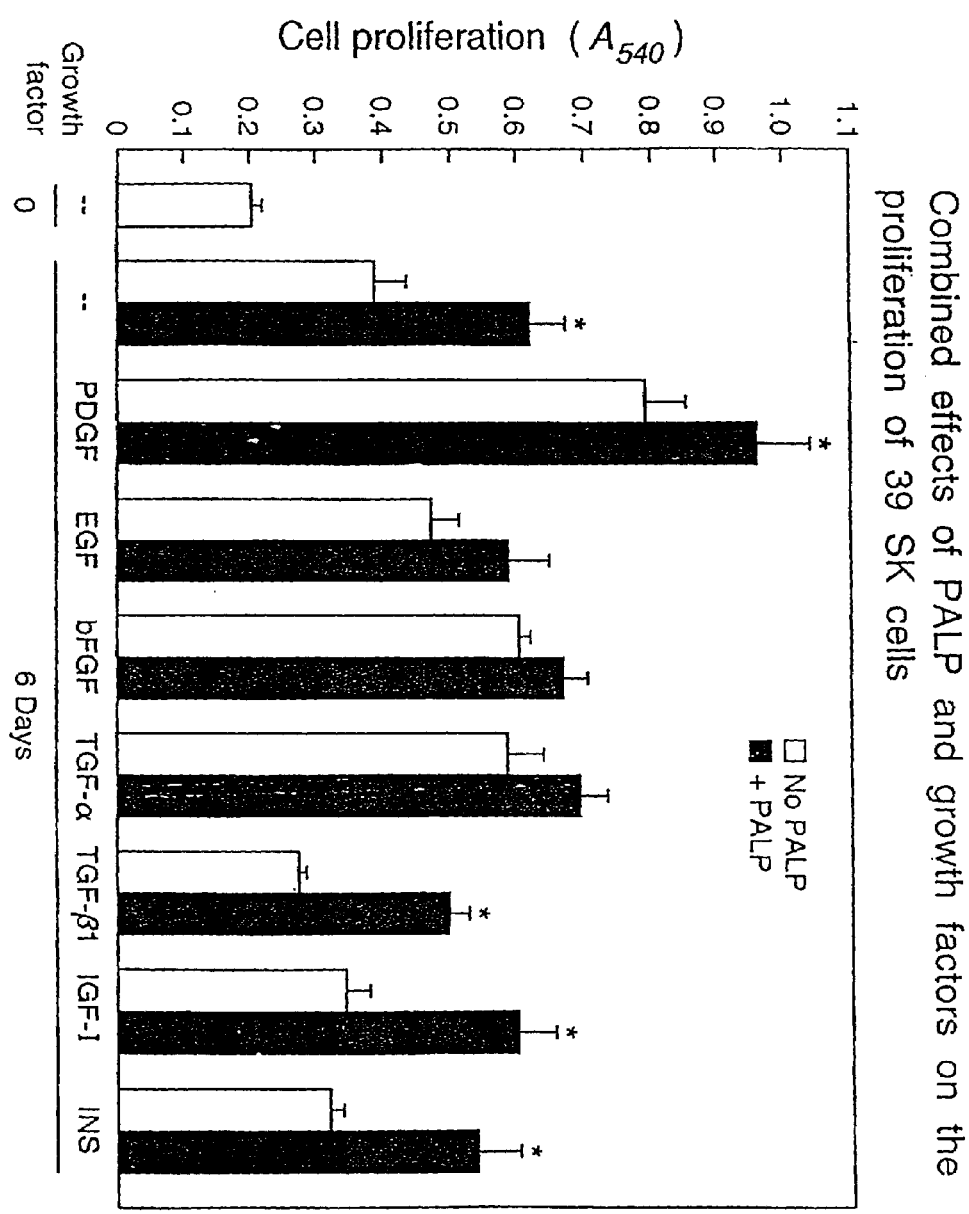
FIG. 7 is a plot of the effect of PALP and growth factors on CC39SK human skin fibroblasts.

FIG. 7 shows a plot of the assay results. At these concentrations, the growth factors had maximal effects on proliferation in CCD 1058 SK fibroblasts, as determined in previous experiments (not shown). Data are the means±S.D. of 8 incubations. As indicated in FIG. 7 with an "*", significantly (P<0.01–0.05 levels) greater cell proliferation was observed in the experiments in the presence of the PALP than in the corresponding experiments in the absence of PALP.

In these cells, PDGF was about twice as effective as PALP in increasing cell proliferation. However, PALP further increased the effect of PDGF, it reversed the inhibitory influence of TGF-β1, and it increased the effects of IGF-I and INS. Overall, PALP had only positive effects on cell proliferation.

Example 7

Effect of PALP with Different Factors in a Second Cell Line

This example relates to determining the effect of PALP, alone and in combination with other factors, on the viability and proliferation of the CCD 986 SK skin fibroblast cell line.

Figure 8:
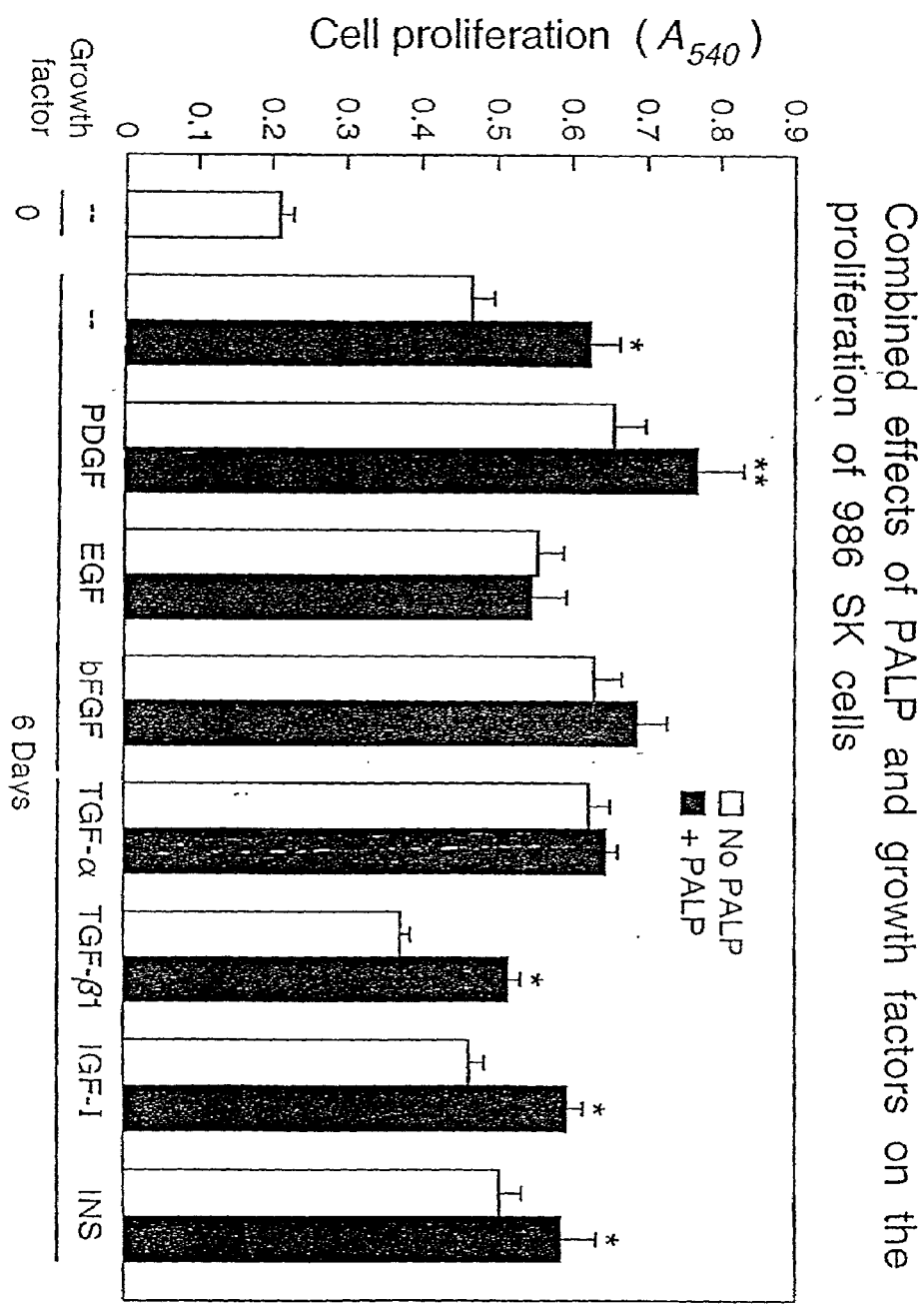
FIG. 8 is a plot of the effect of PALP and growth factors on CC986SK human skin fibroblasts.

CCD 986 SK human skin fibroblast cells, incubated in 1% FCS-containing DMEM for 6 days, were untreated (□) or treated (■) with 0.5 Unit/ml Sigma PALP in the absence or presence of PDGF (50 ng/ml), EGF (50 ng/ml), bFGF (20 ng/ml), TGF-α (50 ng/ml, TGF-β1 (5 ng/ml), IGF-I (50 ng/ml) or INS (500 nM), as indicated. This was followed by the MTT assay. FIG. 8 shows a plot of the assay results. Data are the means±S.D. of 8 incubations. As indicated in FIG. 8 with an "*", significantly (P<0.01–0.05 levels) greater assay values were obtained in the presence of PLAP than the corresponding values in the absence of PALP.

In this cell line, PALP, PDGF, bFGF, and TGF-α were similarly effective stimulators of cell proliferation while TGF-β1 was clearly inhibitory. PALP enhanced the stimulatory effects of PDGF, it retained its stimulatory effects in the presence of IGF-I and INS, and it reversed the inhibitory influence of TGF-β1. Overall, PALP had only positive effects on cell proliferation in this cell line.

Example 8

Effect of PALP with Different Factors in a Third Cell Line

This example relates to determining the effect of PALP, alone and in combination with other factors, on the viability and proliferation of the CCD 1058 SK skin fibroblast cell line.

Figure 9:
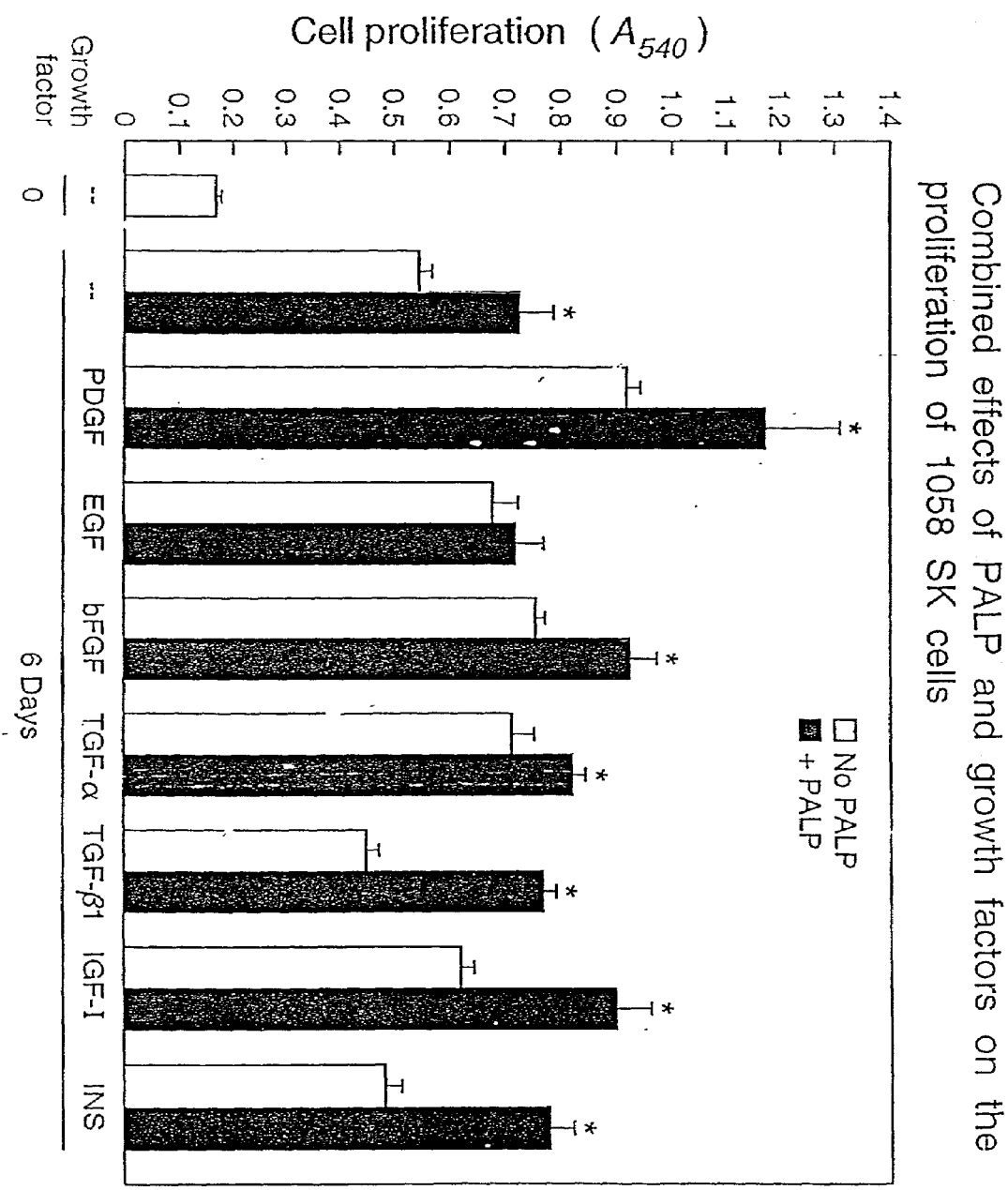
FIG. 9 is a plot of the effect of PALP and growth factors on CC1058SK human skin fibroblasts.

CCD 1058 SK human skin fibroblast cells, incubated in 1% FCS-containing DMEM for 6 days, were untreated (□) or treated (■) with 0.5 Unit/ml Sigma PALP in the absence or presence of PDGF (50 ng/ml), EGF (50 ng/ml), bFGF (20 ng/ml), TGF-α (50 ng/ml), TGF-β1 (5 ng/ml), IGF-I (50 ng/ml) or INS (500 nM), as indicated. This was followed by the MTT assay. FIG. 9 shows a plot of the assay results. Data are the means±S.D. of 8 incubations. As indicated in FIG. 9 with an "*", significantly (P<0.01–0.05 levels) greater values were obtained with PALP present than the corresponding values in the absence of PALP.

In this cell line, PALP was about half as effective as PDGF but as effective as bFGF and TGF-α in enhancing cell proliferation. PALP enhanced the stimulatory effects of PDGF, bFGF, TGF-α, IGF-I, and INS and it effectively reversed the slight inhibitory influence of TGF-β1. Overall, PALP had only positive effects on cell proliferation in this cell line.

Example 9

Effect of PALP with Different Factors in a Fourth Cell Line

This example relates to determining the effect of PALP, alone and in combination with other factors, on the viability and proliferation of the CCD 974 SK skin fibroblast cell line.

Figure 10:
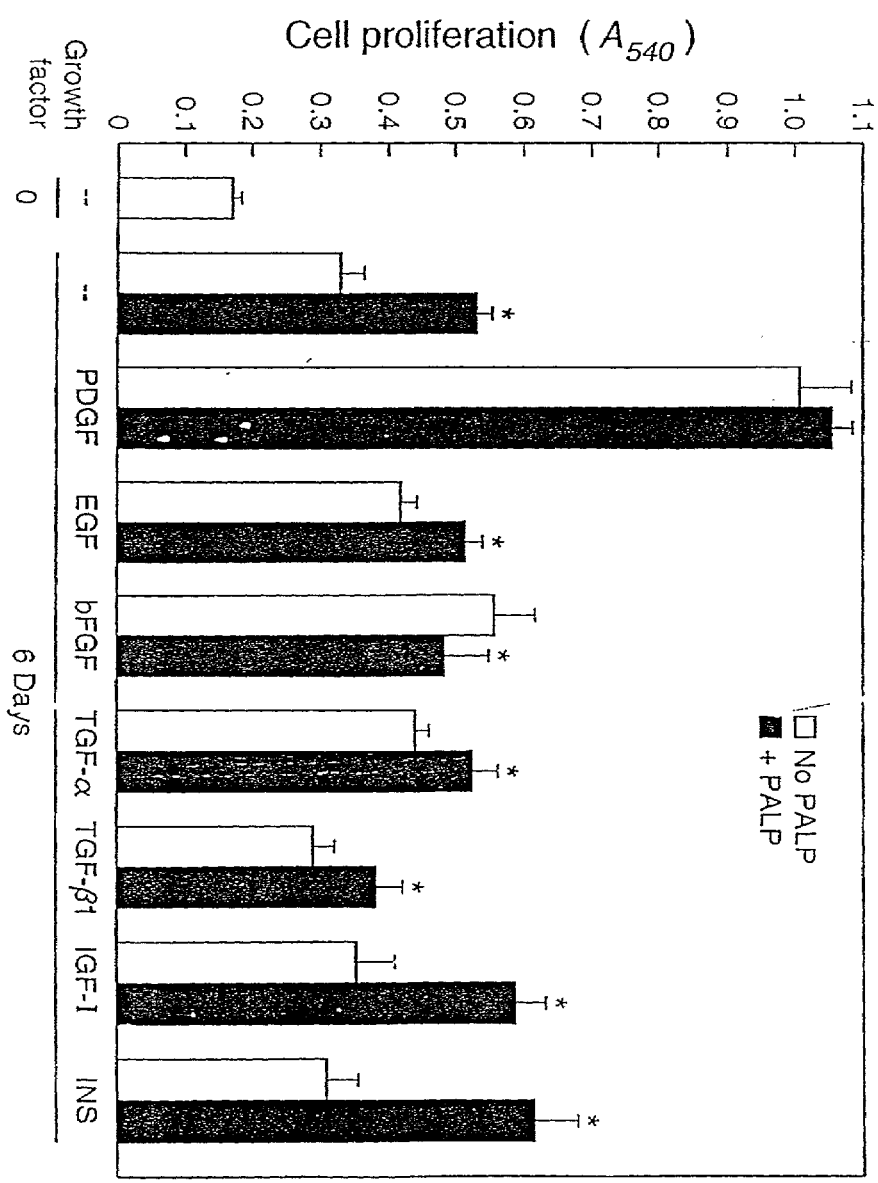
FIG. 10 is a plot of the effect of PALP and growth factors on CC974SK human skin fibroblasts.

CCD 974 SK human skin fibroblasts cells, incubated in 1% FCS-containing DMEM for 6 days, were untreated (□) or treated (■) with 0.5 Unit/ml Sigma PALP in the absence or presence of PDGF (50 ng/ml), EGF (50 ng/ml), bFGF (20 ng/ml), TGF-α) (50 ng/ml), TGF-β1 (5 ng/ml), IGF-I (50 ng/ml) or INS (500 nM), as indicated. This was followed by the MTT assay. FIG. 10 shows a plot of the assay results. Data are the means±S.D. of 8 incubations. As indicated in FIG. 10 with an "*", significantly (P<0.01–0.05 levels) greater values were obtained in the presence of PALP than the corresponding value in the absence of PALP.

This cell line responded very well to PDGF but less well to PALP and the other growth factors. PALP partially reversed the slight inhibitory influence of TGF-β1, it slightly enhanced the stimulatory effects of IGF-I and INS, and it retained its stimulatory effect in the presence of EGF and TGF-α. Overall, PALP had only positive effects on cell proliferation in this cell line.

Example 10

Effect of PALP with Different Factors in a Fifth Cell Line

This example relates to determining the effect of PALP, alone and in combination with other factors, on the viability and proliferation of the CCD 944 SK skin fibroblast cell line.

Figure 11:
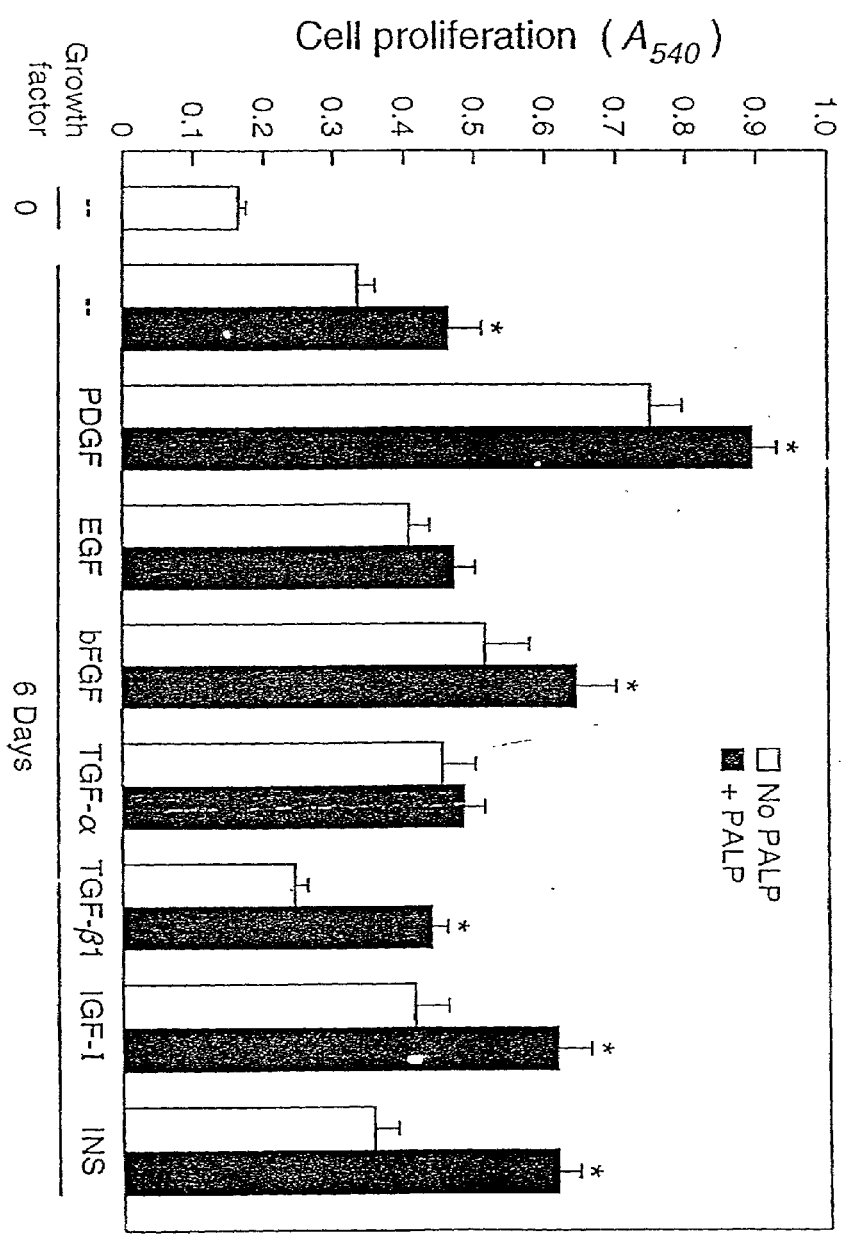
FIG. 11 is a plot of the effect of PALP and growth factors on CC944SK human skin fibroblasts.

CCD 944 SK human skin fibroblast cells, incubated in 1% FCS-containing DMEM for 6 days, were untreated (□) or treated (■) with 0.5 Unit/ml Sigma PALP in the absence or presence of PDGF (50 ng/ml), EGF (50 ng/ml), bFGF (20 ng/ml), TGF-α (50 ng/ml), TGF-β1 (5 ng/ml), IGF-I (50 ng/ml) or INS (500 nM), as indicated. This was followed by the MTT assay. FIG. 11 shows a plot of the assay results. Data are the means±S.D. of 8 incubations. As shown in FIG. 11 with an "*", significantly (P<0.01–0.05 levels) greater values were obtained in the presence of PALP than the corresponding value in the absence of PALP.

In this cell line, PDGF was a more effective inducer of cell proliferation than PALP, while PALP was as effective as bFGF and TGF-α. PALP enhanced the stimulatory effects of PDGF, bFGF, IGF-I, and INS, and it reversed the substantial inhibitory effect of TGF-β1. Overall, PALP had only positive effects on cell proliferation in this cell line.

Example 11

Effect of PALP with Different Factors in a Sixth Cell Line

This example relates to determining the effect of PALP, alone and in combination with other factors, on the viability and proliferation of the CCD 944 SK skin fibroblast cell line.

Figure 12:
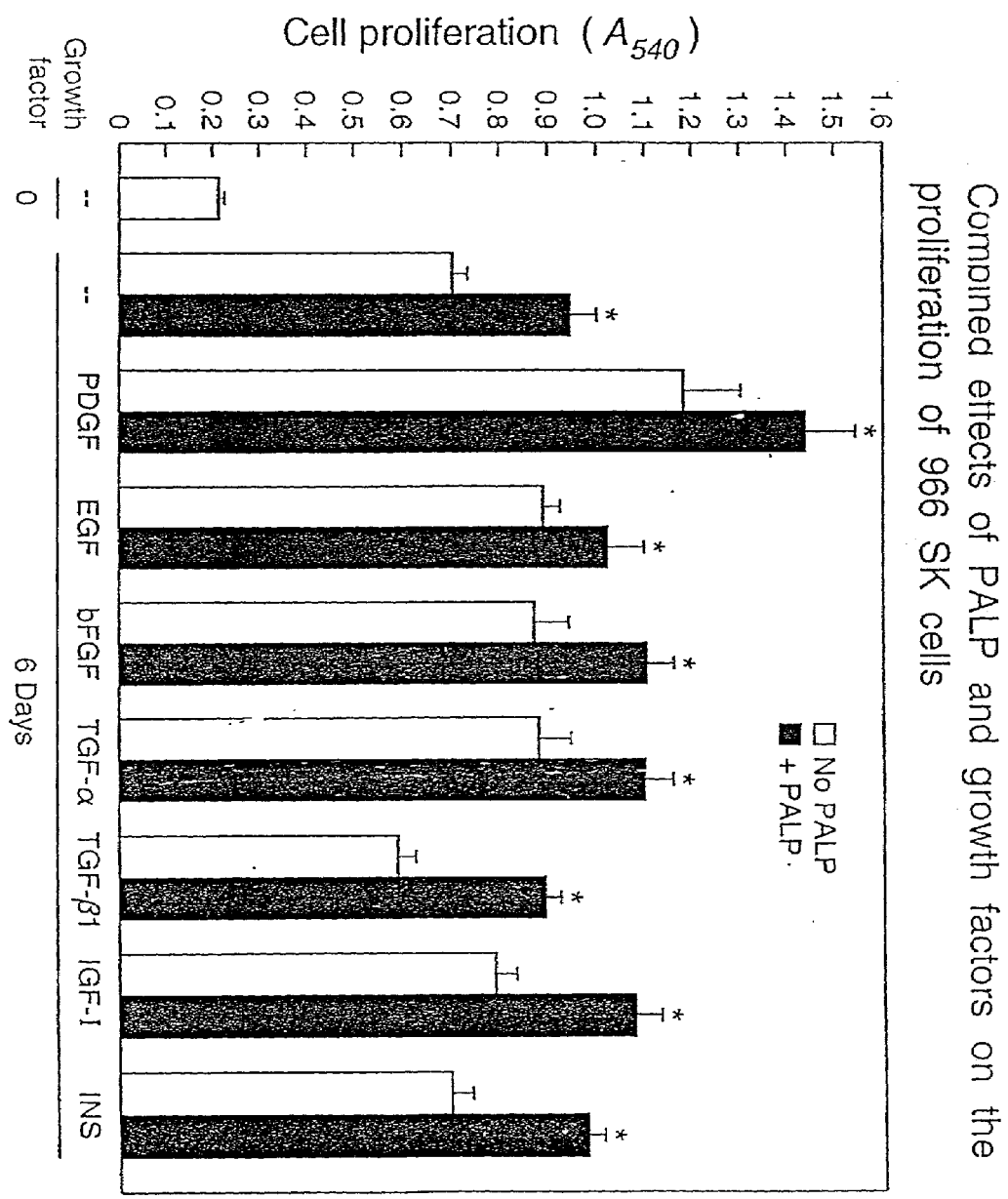
FIG. 12 is a plot of the effect of PALP and growth factors on CC966SK human skin fibroblasts.

CCD 966 SK human skin fibroblast cells, incubated in 1% FCS-containing DMEM for 6 days, were untreated (□) or treated (■) with 0.5 Unit/ml Sigma PALP in the absence or presence of PDGF (50 ng/ml), EGF (50 ng/ml), (bFGF) (20 ng/ml), TGF-α (50 ng/ml), TGF-β1 (5 ng/ml), IGF-I (50 ng/ml) or INS (500 nM), as indicated. This was followed by the MTT assay. FIG. 12 shows a plot of the assay results. Data are the means±S.D. of 8 incubations. As indicated in FIG. 12 with an "*", significantly (P<0.01–0.05 levels) greater values were obtained in the presence of PALP than the corresponding values in the absence of PALP.

In this cell line, PDGF was about twice as effective as PALP in enhancing cell proliferation, while PALP was more effective than the other growth factors. PALP increased the effects of each stimulatory growth factor and it also reversed the inhibitory influence of TGF-β1. Overall, PALP had only positive effects on cell proliferation in this cell line.

Example 12

Determination of Changes in Cell Number

This Example demonstrates that cell counting and MTT assays yield roughly equivalent results for determining the effectiveness of PALP in stimulating fibroblasts.

For the determination of changes in cell numbers, CCD 1058 SK fibroblasts were seeded in 12-well plates in 10% FCS-containing DMEM up to about ~20% confluency. Then, the medium was changed for fresh medium with no serum or supplemented with 2% or 10% FCS. Half of the wells received no further addition, while the other half of the cells were treated with 1 unit/ml PALP; both sets were incubated for 4 days. Cells were stained (Giemsa), then from each well 3 photographs were taken, and finally cells were counted manually.

In cell proliferation studies, after treatments for 4 days, in serum-free medium PALP had practically no effects, while in the presence of 2% and 10% FCS it enhanced cell numbers 39 and 33%, respectively. Parallel studies using the MTT viability assay (see above) showed that PALP had no effects in the absence of FCS, while in the presence of 2% and 10% FCS it increased the number of viable cells 44% and 30%, respectively. Since the experimental error was between 5–10%, it was concluded that in case of PALP, cell counting and the MTT assay provide practically the same results (i.e. suggesting that PALP does not alter the cellular oxidation/reduction events), i.e. that increased formazan production is proportional with increased cell numbers.

Example 13

Collagen Synthesis in the presence of PALP

This example relates to evaluating the amount of collagen synthesis in skin fibroblasts in the presence of PALP.

Figure 13:
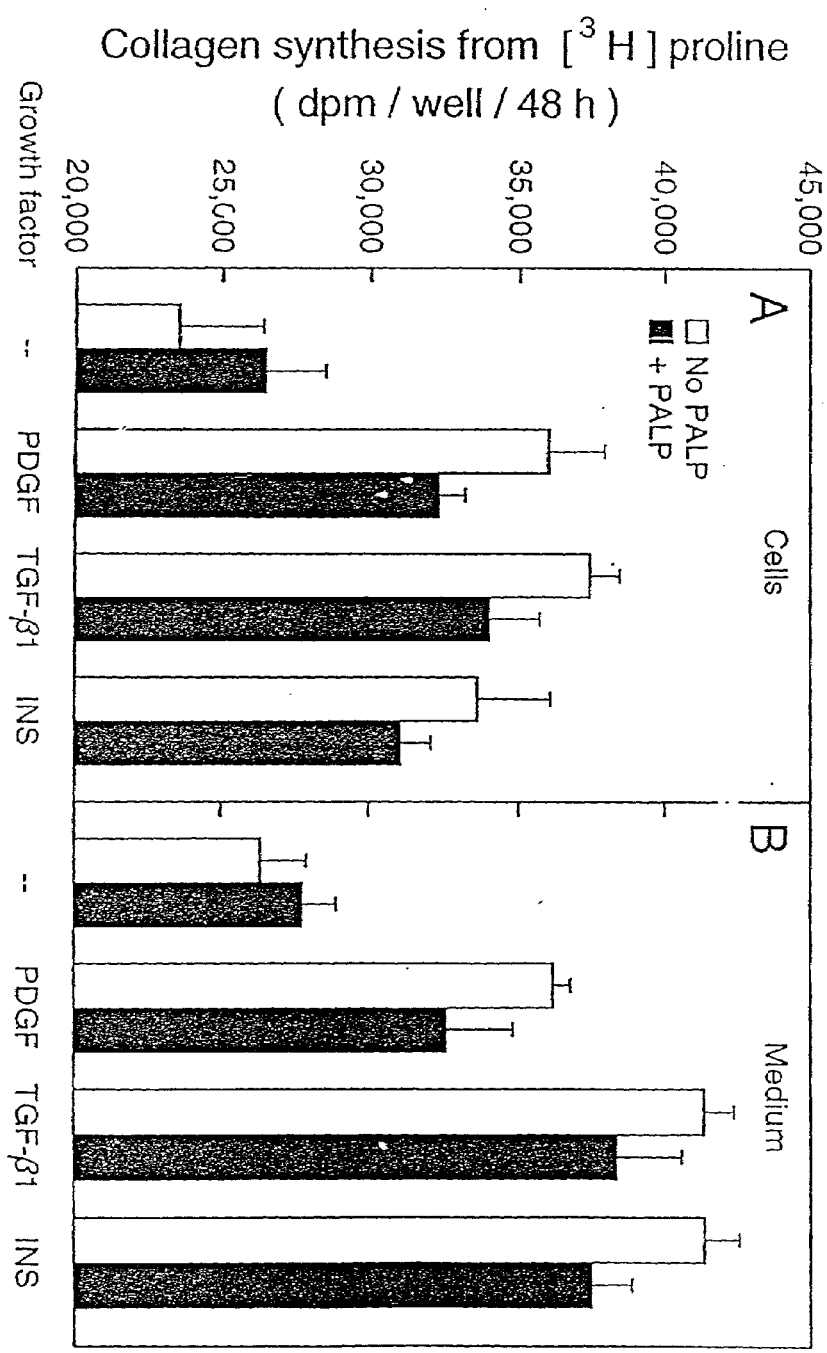
FIG. 13 is a plot of the effect of PALP and various growth factors on the amount of collagen in cells and media.

The method used here for determination of collagen synthesis is widely used and well accepted in the art. Fibroblasts at 80% confluency were incubated (in 6-well plates) in 1% FCS-containing DMEM for 48 h with [2,3-$^3$H]proline (4 $\mu$Ci/well), ascorbic acid (50 $\mu$g/ml) and $\beta$-aminoproprionitrile (50 $\mu$g/ml); other agents present are indicated in FIG. 13. After incubations, the medium was harvested and the cells were washed with phosphate buffered saline and trypsinized in 0.5 ml 50 mM Tris-HCl, pH 7.6. Cells were sonicated and then incubated with ribonuclease (5 $\mu$g/sample; 10 min). Proteins from both the cells and medium were precipitated with 10% trichloroacetic acid (TCA). The precipitate was washed with 5% TCA, and the pellet was dissolved in 0.5 ml 0.2 M NaOH. The samples were neutralized with 0.1 ml Hepes buffer, 120 mM (pH 7.2, containing 12.5 mM N-ethyl maleimide and 2.5 mM $CaCl_2$), and 0.16 ml of 0.15 M HCl, followed by collagenase (20 units/ml) treatment for 90 min at 37° C. Then, proteins were precipitated by an equal volume of TCA/tannic acid (10% and 0.5%, respectively) and the supernatant was collected. The precipitate was washed again and the supernatants were combined. The counts from samples without collagenase treatment were determined and subtracted from that measured from collagenase-treated samples to estimate the amount of synthesized collagen.

To obtain collagen sysnthesis results for PALP treated fibroblasts, CCD 1058 SK cells were incubated in 1% FCS for about 48 hours. During the whole incubation period, the incubation medium contained [$^3$H]proline and the cells were treated with 50 ng/ml PDGF, 5 ng/ml TGF-$\beta$1, or 500 nM INS, as indicated, in the absence ($\rho$) or presence (v) of 1 Unit/ml Sigma PALP. The amount of [$^3$H]collagen was determined both in the cells (A) and in the medium (B). Data are the means±S.D. of 3 independent incubations. FIG. 13 shows a plot of the assay results.

Each growth factor shown, but not PALP, considerably enhanced collagen synthesis, with 50% or more collagen being secreted into the medium. The growth factors did not appear to specifically stimulate collagen secretion. PALP alone had no stimulatory effects, while it moderately, but invariably, reduced the effects of growth factors on both collagen synthesis and on the collagen content in the medium.

The embodiments above are intended to be exemplary and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. A composition for skin wound healing in a patient comprising placental alkaline phosphatase in an amount effective for stimulating proliferation of fibroblasts and a gel-forming material, wherein said composition is formulated for topical delivery.

2. The composition of claim 1 further comprising a growth factor or a growth promoting serum factor.

3. The composition of claim 1 further comprising a growth factor selected from the group consisting of PDGF, EGF FGF, TGF-$\alpha$, IGF-I, insulin and combinations thereof.

4. The composition of claim 1 further comprising serum.

5. The composition of claim 1 further comprising an growth promoting serum factor.

6. The composition of claim 1 wherein the gel-forming material is selected from the group consisting of methyl cellulose, agar, agarose, gelatin, calcium algenate and combinations thereof.

7. The composition of claim 1 wherein the concentration of the placental alkaline phosphatase is between about 0.001 and about 1 mg/1 gram product.

8. The composition of claim 1 wherein the concentration of the placental alkaline phosphatase is between about 0.01 and about 0.5 mg/1 gram product.

9. The composition of claim 1 further comprising an additive selected from the group consisting of a preservative, a buffer, an antibiotic and a moisture controller.

10. The composition of claim 1, wherein the composition is a gel, a lotion, a cream, a rinse, a foam, a mousse, or a spray.

11. The composition of claim 1, wherein the composition further comprises PDGF.

12. The composition of claim 11, wherein the composition further comprises insulin.

* * * * *